United States Patent [19]

Crawford et al.

[11] Patent Number: 4,559,326

[45] Date of Patent: Dec. 17, 1985

[54] ANTIINFLAMMATORY COMPOSITIONS AND METHODS

[75] Inventors: Thomas C. Crawford; Stanley L. Keely, both of Ledyard; David L. Larson, East Lyme; Joseph G. Lombardino, Niantic; James J. Maciejko, Mystic, all of Conn.

[73] Assignee: Pfizer Inc., New York, N.Y.

[21] Appl. No.: 696,686

[22] Filed: Jan. 31, 1985

[51] Int. Cl.⁴ .................... A61K 31/70; A61K 31/605
[52] U.S. Cl. ...................................... 514/23; 514/164; 514/224; 514/420; 514/557
[58] Field of Search ................... 424/246; 514/23, 224

[56] References Cited

FOREIGN PATENT DOCUMENTS 7308869 10/1974 France .

*Primary Examiner*—Stanley J. Friedman
*Attorney, Agent, or Firm*—Charles J. Knuth; Albert E. Frost; Robert K. Blackwood

[57] ABSTRACT

An improved antiinflammatory composition and method of treating inflammation which employs a combination of a non-steroidal antiinflammatory agent such as prioxicam, or a pharmaceutically acceptable salt thereof, with inositol.

4 Claims, No Drawings

ANTIINFLAMMATORY COMPOSITIONS AND METHODS

BACKGROUND OF THE INVENTION

The present invention is concerned with an improved antiinflammatory composition and method of treating inflammation which employs a non-steroidal antiinflammatory agent such as piroxicam, or a pharmaceutically acceptable salt thereof (particularly the ethanolamine salt of piroxicam), in combination with inositol. The generic names used here and elsewhere herein are from the USAN and the USP Dictionary of Drug Names, 1961-1981, Griffiths et al., ed., U.S. Pharmacopeial Convention Inc., Rockville, Md., 1984, have subsequently been assigned and published as official USAN names, and/or appear in The Merck Index 10th Edition.

Gastrointestinal irritation, including ulcers, is a side effect commonly associated, to one degree or another, with antiinflammatory agents. In many cases, individuals requiring such antiinflammatory treatment are precluded from enjoying the benefits thereof because of their susceptibility to such side effects. The present combination of a non-steroidal antiinflammatory agent with inositol permits desirable antiinflammatory therapy while preventing or ameliorating said gastrointestinal irritation or ulcers.

Inositol is an optically inactive, meso compound systematically named cis-1,2,3,4-trans-4,6-cyclohexanehexol, also called meso-inositol or bios I (see The Merck Index 10th Ed., abstract no. 4861). It has long been known as a growth factor for micoorganisms (see, for example, Fieser and Fieser, "Organic Chemistry", Heath and Co., Boston, 1944, pp. 654-5). However, there are no known reports bearing on the use of inositol to reduce gastric side effects of nonstereoidal antiinflammatory agents or to reduce the frequency of ulcers in any circumstances.

SUMMARY OF THE INVENTION

The present invention concerns an improved antiinflammatory composition which comprises an antiinflammatory amount of a compound selected from the group consisting of aspirin, carprofen, diclofenac, diflunisal, etodolac, fenoprofen, fentiazac, flurbiprofen, ibuprofen, indomethacin, isoxicam, ketoprofen, meclofenamic acid, naproxen, niflumic acid, oxaprozin, piroxicam, piroprofen, sulindac, suprofen, tenoxicam and tolmetin; and the pharmaceutically acceptable salts thereof (particularly the ethanolamine salt of piroxicam), in combination with a gastric antiirritation and ulcer inhibiting amount of inositol.

The present invention is also concerned with an improved method for the treatment of inflammation in a mammal, including man, which comprises, in addition to treatment with an antiinflammatory amount of an antiinflammatory agent as listed above, treatment with a gastric antiirritation and ulcer inhibiting amount of inositol.

DETAILED DESCRIPTION OF THE INVENTION

Like inositol, the antiinflammatory agents of the present invention are known. For example, The Merck Index 10th Ed., 1983 contains a monograph concerning piroxicam (no. 7378), as does the Physicians' Desk Reference (PDR), 38th Ed., pp. 1556-1557 (1984). The preferred ethanolamine salt of piroxicam is specifically disclosed in U.S. Pat. No. 4,434,164. The Merck Index 10th Ed. also contains monographs on aspirin (no. 863), carprofen (no. 1846), diclofenac sodium (no. 3066), diflunisal (no. 3127), etodolac (no. 3822), feoprofen (no. 3913), fentiazac (no. 3928), fluriprofen (no. 4101), ibuprofen (no. 4797), indomethacin (no. 4852), isoxicam (no. 5085), ketoprofen (no. 5142), melofenamic acid (no. 5600; the sodium salt is named meclofenamate sodium), naproxen (no. 6269), niflumic acid (no. 6377), oxaprozin (no. 6797), pirprofen (no. 7380), sulindac (no. 8863), suprofen (no. 8889), tenoxicam (no. 8980) and tolmetin (no. 9346).

The clinical value of the present improved formulation is inhibiting gastric irritation and ulcers induced by antiinflammatory agents is reflected by appropriate animal studies. A typical experimental protocol, in which the ability of the test compound to prevent or reduce such induced gastric lesioning was determined, is found in the specific Examples below.

The present invention is readily carried out. The antiinflammatory agent or its salt is dosed in a mammal, particularly man, in its usual range, e.g., piroxicam is generally dosed in the range of 0.1 to 1 mg/kg/day, while indomethacin is generally dosed in the range 0.4-4 mg/kg/day with the usual frequency of dosage (e.g., generally a single daily dose in the case of piroxicam and a divided daily dose in the case of indomethacin). The inositol, which if desired can be dosed separately in single or multiple daily dosage, is generally dosed in the range of 0.06-40 mg/kg/day.

Preferably and conveniently, the antiinflammatory agent and the inositol are co-administered in a single, combined formulation. This can be in a form suitable for parenteral administration, but is preferably in a form suitable for oral administration. The proportion of each drug in the combined dosage form will be in the ratio of the total daily dosage of each drug when dosed alone, in amounts suitable for single or divided daily doses as appropriate. The combined drugs will be dosed in single or divided doses. Single daily dosage will be most preferred in those cases where the in vivo half-life of the antiinflammatory agent is (like that of piroxicam) relatively long.

In the preferred oral route of dosage, the amount of piroxicam (or salt equivalent) for an average adult patient will generally be in the range of 5-50 mg/day in combination with 20 to 2000 mg/day of inositol, an amount generally sufficient to inhibit gastrointestinal irritation or ulcers which could otherwise be induced by the piroxicam in patients susceptible to this side effect.

The combined compounds are administered alone or in further combination with pharmaceutically-acceptable carriers or diluents. For oral use, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tables containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

The present invention is illustrated by the following examples. However, it should be understood that the invention is not limited to the specific details of these examples.

EXAMPLE 1

Protective Effect of Inositol on Piroxicam-Induced Gastric Lesions in Rats

Adult male "specific pathogen free" rats weighing 140–160 grams of the CD strain (Sprague-Dawley) were obtained from Charles River Breeding Laboratories (Kingston, N.Y.). The animals were acclimated for approximately one week and tested when they reached a body weight of 200–225 grams. The rats were fasted for 16 hours and randomized into groups consisting of 8 to 20 animals which were normalized with regard to their average body weight.

Gastric ulcers were induced in the animals by orally dosing them with a single 120 mg/kg dose of piroxicam (ethanolamine salt) in 2 ml. of aqueous 0.1% methylcellulose (pH=6.8). Those animals receiving a second medicinal agent separately received the second drug in an additional 2 ml. of the same medium at about the same time. Six and one-half hours later, the animals were sacrificed by cervical dislocation and autopsied. The stomachs were surgically removed, dissected along the greater curvature and rinsed with cold water. The stomachs were individually scored for both linear and punctate lesions. The total number of lesions was used for scoring purposes. The data obtained from each group of rats were analyzed after calculation of the mean number $+/-$ the standard error of total gastric lesions. The values obtained were also compared to the controls which received only piroxicam by the two-tailed Student's T-Test for nonpaired data. The protective effect of inositol against piroxicam-induced ulcers is shown in Table I. These data show that inositol significantly reduces piroxicam-induced gastric lesions in the healthy fasted rat.

TABLE I

Protective Effect of Inositol on Gastric Lesions Induced by the Ethanolamine Salt Salt of Piroxicam

| Form of Vitamin B6 | Oral Dose (mg/kg) | No. of Rats in Group | Lesions/Rat ($\overline{X} +/-$ SE)[b] | Significance $p < 0.05$[c] |
|---|---|---|---|---|
| (Control)[a] | 0 | 30 | 7.5 (0.8) | |
| Inositol[a,d] | 10 | 40 | 4.7 (0.9) | + |
| | 33 | 40 | 5.2 (0.7) | + |
| | 100 | 40 | 3.6 (0.6) | + |
| | 333 | 40 | 3.0 (0.8) | + |

[a]All animals, including controls, received 120 mg/kg of the ethanolamine salt of piroxicam.
[b]Represents the mean value $\overline{X} +/-$ the standard error (SE).
[c]As determined by the Student's two tailed T-test for non-paired data.
[d]As calculated by linear regression analysis, an ED50 (dose of inositol required to inhibit 50% of control gastric lesion) of 85 mg/kg was determined.

EXAMPLE 2

Capsules—Piroxicam (20 mg) and Inositol (1000 mg)

The following ingredients are combined in the following proportions by weight:

| | |
|---|---|
| piroxicam (milled) | 20 |
| inositol (milled) | 1000 |
| calcium carbonate | 250 |
| polyethylene glycol, average molecular weight, 4000 | 430 |

The mixture is thoroughly blended so as to obtain a uniform powder. Soft gelatin capsules containing 20 mg. of piroxicam and 1000 mg. of inositol are prepared by filling suitably sized capsules with 1700 mg of the blend.

To make hard gelatin filled capsules, the amount of inert ingredients is adjusted so as to conveniently fill standard sized gelatin capsules containing the desired amount of each active component.

EXAMPLE 3

Capsules—Piroxicam (10 mg) and Inositol (500 mg)

The following ingredients are combined in the following proportions by weight:

| | | |
|---|---|---|
| piroxicam ethanolamine salt (milled) | 11.84 | (equivalent to 10 as free acid) |
| inositol (milled) | 500 | |
| corn starch | 484.16 | |
| magnesium stearate | 4 | |

The mixture is thoroughly blended so as to form a uniform powder. The resultant mix is filled into appropriately sized hard gelatin capsules (fill weight 1000 mg) so as to obtain capsules containing the desired potency of each active ingredient.

EXAMPLE 4

Capsules—Piroxicam (20 mg) and Inositol (150 mg)

The following ingredients are combined in the following proportions by weight:

| | |
|---|---|
| piroxicam (milled) | 20 |
| inositol | 150 |
| polyethylene glycol, average molecular weight, 4000 | 630 |

The mixture is thoroughly blended so as to obtain a uniform powder. The resultant mix (800 mg fill weight) is filled into hard gelatin capsules of a suitable size so as to obtain capsules of the desired potency.

EXAMPLE 5

Tablets—Indomethacin (20 mg) and Inositol (20 mg)

The following ingredients are combined in the following proportions by weight:

| | |
|---|---|
| indomethacin (milled) | 20 |
| inositol (milled) | 20 |
| lactose | 183 |
| hydroxypropyl methylcellulose | 3 |
| sodium starch glycollate | 15 |
| magnesium stearate | 4 |

The mixture is thoroughly blended to form a uniform powder. Measured volumes of the powder, corresponding to 250 mg by weight, are compressed into tablets containing the desired potency of each active ingredient.

EXAMPLE 6

Tablets—Piroxicam (10 mg) and Inositol (25 mg)

The following ingredients are combined in the following proportions by weight:

| | | |
|---|---|---|
| piroxicam ethanolamine salt (milled) | 11.84 | (equivalent to 10 of free base) |
| inositol | 25 | |
| lactose | 238.16 | |
| hydroxypropyl methylcellulose | 4 | |
| sodium starch glycollate | 16 | |
| magnesium stearate | 5 | |

The mixture is throughly blended to form a uniform powder. The powder, in measured volumes corresponding to 300 mg. by weight, is compressed into tablets containing the desired potency of each active ingredient.

EXAMPLE 7

Tablets—Piroxicam (20 mg) and Inositol (50 mg)

The following ingredients are combined in the following proportions by weight:

| | |
|---|---|
| piroxicam | 20 |
| inositol | 50 |
| lactose | 250 |
| hydroxypropyl methylcellulose | 4 |
| sodium starch glycollate | 16 |
| magnesium stearate | 5 |

The mixture is blended to a uniform powder and compressed into tablets in measured volumes corresponding to 345 mg by weight to yield tablets of the desired potency in each drug.

We claim:

1. A method of treating inflammation in a mammal which comprises administration of a mammal in need for such treatment:
   (a) an antiinflammatory amount of piroxicam, or a pharmaceutically acceptable salt thereof; and
   (b) a gastric antiirritation and ulcer-inhibitory amount of inositol.

2. The method of claim 1 wherein the piroxicam is in the form of its ethanolamine salt.

3. An improved antiinflammatory composition which comprises:
   (a) an antiinflammatory amount of piroxicam or a pharmaceutically acceptable salt thereof; and
   (b) a gastric antiirritation and ulcer-inhibiting amount of inositol.

4. The composition of claim 1 wherein the piroxicam is in the form of its ethanolamine salt.

* * * * *